United States Patent [19]

Koizumi et al.

[11] 4,435,202

[45] Mar. 6, 1984

[54] PLANT GROWTH REGULATOR

[75] Inventors: Masuo Koizumi, Tokyo; Norio Shirakawa, Saitama; Hiromi Tomioka, Tokyo; Masaki Takeuchi; Masanori Okada, both of Saitama; Masahiro Yoshimoto; Yasushi Murakami, both of Tokyo; Yoshitaka Iwane, Kanagawa, all of Japan

[73] Assignee: Chugai Seiyaku Kabushiki Kaisha, Tokyo, Japan

[21] Appl. No.: 363,023

[22] Filed: Mar. 29, 1982

Related U.S. Application Data

[62] Division of Ser. No. 137,894, Apr. 7, 1980, abandoned.

[30] Foreign Application Priority Data

Apr. 19, 1979 [JP] Japan .................................. 54-47299

[51] Int. Cl.³ ............................................ A01N 43/40
[52] U.S. Cl. .......................................... 71/76; 71/90; 71/94; 546/323; 549/59
[58] Field of Search ........................................ 71/76, 94

[56] References Cited

U.S. PATENT DOCUMENTS

| | | | |
|---|---|---|---|
| 3,340,042 | 9/1967 | Schwartz et al. | 71/94 |
| 4,137,067 | 1/1979 | Gätzi | 71/94 |
| 4,193,788 | 3/1980 | Shudo et al. | 71/94 |
| 4,195,984 | 4/1980 | Stein et al. | 71/94 |
| 4,225,336 | 9/1980 | Fory et al. | 71/94 |
| 4,240,823 | 12/1980 | Clapot et al. | 71/94 |
| 4,284,566 | 8/1981 | Böhner et al. | 71/94 |
| 4,377,407 | 3/1983 | Shirakawa et al. | 71/76 |

FOREIGN PATENT DOCUMENTS

| | | | |
|---|---|---|---|
| 630669 | 11/1961 | Canada | 71/94 |
| 46-10882 | 3/1971 | Japan | 71/94 |
| 53-72825 | 6/1978 | Japan | 546/323 |

OTHER PUBLICATIONS

Petyunin et al., "X. The Magnesylamine Method, etc.," (1962) J. Gen. Chem. USSR 33 pp. 1232–1234 (1963).
Hosoda et al., "Isonicotionamilide Fungicides," (1978) CA 90 No. 1676 v. (1979).

Primary Examiner—Glennon H. Hollrah
Attorney, Agent, or Firm—Browdy & Neimark

[57] ABSTRACT

A plant growth regulator containing as an active ingredient one or more compounds represented by the formula

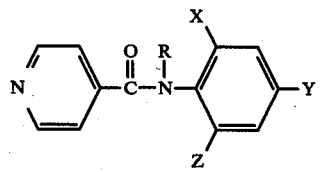

wherein R, X, Y and Z are defined in the specification is disclosed. The plant growth regulator is effective for a wide variety of plants, particularly for grassy plants. In addition to such activity, the regulator of this invention acts on plants to thicken the foliage and to aid health growth without causing substantial phytotoxicity.

6 Claims, No Drawings

PLANT GROWTH REGULATOR

This is a division of application Ser. No. 137,894 filed Apr. 7, 1980, now abandoned.

This invention relates to a plant growth regulator which contains as an active ingredient one or more compounds represented by the formula

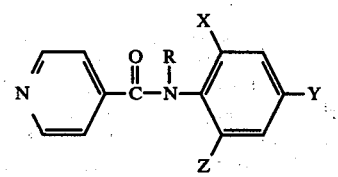

wherein R is hydrogen, lower alkyl, or p-chlorobenzyl; X is hydrogen or a halogen; Y is hydrogen, a halogen, methyl or nitro, Z is hydrogen, a halogen, benzoyl, or 3-thenoyl. The plant growth regulator of this invention is effective for a wide variety of plants, particularly for grassy plants.

The inventors of this invention have searched for several years to find compounds capable of regulating the growth of various plants, and found that isonicotinanilides represented by the formula (I) have excellent growth regulating activity, particularly with respect to grassy plants. On the basis of this fact, they have continued their study to complete this invention.

The compounds of this invention can be advantageously applied to rice plants to inhibit useless unproductive growth, and excess aging in a bed for rice seedling, and to inhibit falldown in paddy field. Also, they inhibit undesirable unproductive growth or falldown of wheat, barley, corn, sugar cane or the like.

In addition to the crops above, the compounds are advantageously applied to lawn. Lawn is widely used in private and public gardens, golf links, green zones or greenbelts, the edge of roads, and the like. However, lawn is troublesome and costly to take care of; this is especially true in the summer when mowing must be done frequently because of rapid growth of the lawn and, therefore, is very expensive.

Also, various grassy plants other than lawn are planted on the edge or shoulder of roads or highways, greenbelts, highway or railroad banks, or the like. Taking care of these plants is not only costly and laborious, but also is very dangerous. Thus, the application of the compounds of this invention to these plants is very advantageous.

The compounds of this invention can be used to regulate the growth of broadleaf plants and as a result of the regulation of growth, an improvement in resistance to poor growing circumstances and various pests can be expected.

Furthermore, the application of the compounds of this invention to crops increases the amount of chlorophyl in leaves to accelerate the photosynthesis activity and to promote the production of carbohydrate.

A great advantage of this invention is that the compounds of this invention regulate the growth of plants, particularly the height of plants, and thicken the foliage and aid healthy growth without causing phytotoxicity such as leaf burn or foliage burn whatever type of treatment such as seed treatment, soil treatment or foliage treatment is selected.

The active compounds of this invention are prepared, for example, by the process illustrated by the equation below:

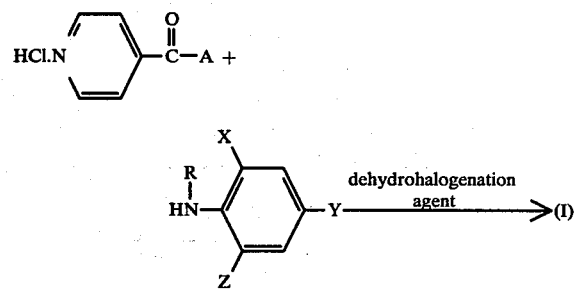

wherein A is a halogen, and R, X, Y and Z are as defined above.

The above reaction is carried out in an inert solvent. The reaction temperature is usually in the range of from about 0°–40° C., but, if necessary, it may be a temperature higher than 40° C. The dehydrohalogenation agent to be used in this invention is selected, depending on the reaction conditions, from a caustic alkali, an alkali carbonate, an organic amine or the like. The reaction is further illustrated by the following exemplary Preparation.

PREPARATION OF COMPOUND 1

Triethylamine (2 g) was added to a solution of 2-benzoyl-4-bromoaniline (2.76 g) in acetone (50 ml) at room temperature. Isonicotinyl chloride hydrochloride (1.76 g) was added slowly to the mixture while cooling it with ice-water to maintain its temperature below 5° C. After completion of the addition, the mixture was stirred at 30° C. for one hour and then acetone was distilled off under reduced pressure. Triethylamine hydrochloride was removed from the residue by addition of water and the remaining crystals were collected by filtration, dried and recrystallized from ethyl acetate to give 2-benzoyl-4-bromoisonicotinanilide. (Yield, 87%; m.p. 137°–138° C.)

Analysis: Calcd. for $C_{19}H_{13}N_2O_2Br$: C, 59.86; H, 3.44; N, 7.35 (%). Found: C, 59.91; H, 3.21; N, 7.46 (%).

Several exemplary compounds listed in Table 1 below and represented by the formula 1 were prepared as in the preparation of Compound 1. The reference number each of the compounds is used hereunder to identify the specific compound.

TABLE 1

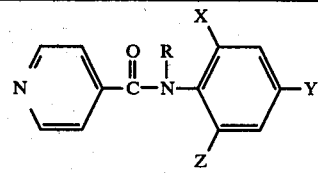

| Compounds | Substituents | | | | m.p. (°C.) |
|---|---|---|---|---|---|
| | R | X | Y | Z | |
| 1 | H | H | Br | —C(O)—C₆H₅ | 137–138 |
| 2 | H | H | CH₃ | —C(O)—C₆H₅ | 110–111 |

TABLE 1-continued

Structure: Pyridine-C(=O)-N(R)-phenyl with substituents X (ortho), Y (para), Z (ortho)

| Compounds | R | X | Y | Z | m.p. (°C.) |
|---|---|---|---|---|---|
| 3 | H | H | NO$_2$ | $-\text{OC}(=O)\text{-phenyl}$ | 142–143 |
| 4 | H | H | H | $-\text{OC}(=O)\text{-phenyl}$ | 98–99 |
| 5 | H | H | Cl | $-\text{OC}(=O)\text{-phenyl}$ | 154–155 |
| 6 | CH$_3$ | H | Cl | $-\text{OC}(=O)\text{-phenyl}$ | 152–153 |
| 7 | C$_2$H$_5$ | H | Cl | $-\text{OC}(=O)\text{-phenyl}$ | 143–144 |
| 8 | H | H | Cl | $-\text{OC}(=O)\text{-thienyl}$ | 178–179 |
| 9 | H | Cl | Cl | H | 119–120 |
| 10 | H | Cl | Cl | Cl | 138–139 |
| 11 | $-\text{CH}_2\text{-C}_6\text{H}_4\text{-Cl}$ | H | Cl | $-\text{OC}(=O)\text{-phenyl}$ | 80–81 |
| 12 | H | Br | Br | Br | 119–120 |
| 13 | H | H | I | $-\text{OC}(=O)\text{-phenyl}$ | 176–177 |

In accordance with this invention, the plant growth regulator is applied to plants in any suitable dose, usually in a dose such that a compound of the formula (I) or a mixture of two or more compounds of the formual (I) is 50–2,000 g/10 ares, preferably 200–1,000 g/10 ares, although the dose of the regulator may very depend on the species and growth level of the plants to be regulated.

The compounds of this invention can be formulated in a conventional way using a solid or liquid carrier commonly used in the formulation of agricultural compositions into wettable powder, emulsion, oil, dust, granules or the like. According to the necessity, a conventional adjuvant, such as dispersant, diluent, emulsifier, penetrating agent, binder or the like may be added. Further, a herbicidal compound, fungicidal compound, insecticidal compound, other plant growth regulator, fertilizer or the like may be incorporated into the formulation of this invention.

The activities of the plant growth regulator of this invention were confirmed by the following Experiments.

EXPERIMENT 1

Growth Regulating Test for Grassy Plants by Pre-emergence Soil Treatment

A pot with the open area of 1/5000 are was filled with dry clayish loam, seeded with bentgrass, Kentucky bluegrass, wild lawn, timothy, Kentucky-31 fescue, barnyard grass, crabgrass, rice, or corn, and lightly covered with the same soil. The pot was sprayed with an aqueous dispersion of the wettable powder formulated in Example 1 in a dose of 250 g or 500 g of the active compound per 10 ares by using a portable sprayer. Fifty days after spraying, the height of the plant in connection with each pot was observed.

The results are shown in Table 2 below.

The degree of growth regulating activity for each plant was rated on the following scale.

0: 0–10% growth control effect in height in terms of untreated section
1: 11–20% growth control effect in height
2: 21–30% growth control effect in height
3: 31–40% growth control effect in height
4: 41–50% growth control effect in height
5: more than 51% growth control effect in height

TABLE 2

| Test Compounds | Dose (g/10a) | Bentgrass | Kentucky bluegrass | Wild Lawn | Timothy | Kentucky-31 fescue | Barnyard grass | Crabgrass | Rice | Corn | Injury |
|---|---|---|---|---|---|---|---|---|---|---|---|
| 1 | 500 | 5 | 5 | 5 | 5 | 5 | 5 | 5 | 3 | 3 | none |
|   | 250 | 5 | 5 | 5 | 5 | 4 | 5 | 5 | 2 | 2 | " |
| 2 | 500 | 3 | 2 | 2 | 2 | 2 | 3 | 3 | 1 | 1 | " |
|   | 250 | 1 | 1 | 0 | 0 | 2 | 1 | 2 | 0 | 0 | " |
| 3 | 500 | 4 | 4 | 3 | 2 | 2 | 3 | 4 | 2 | 0 | " |
|   | 250 | 3 | 2 | 1 | 2 | 1 | 2 | 2 | 0 | 0 | " |
| 4 | 500 | 3 | 3 | 1 | 2 | 2 | 3 | 3 | 1 | 1 | " |
|   | 250 | 2 | 2 | 1 | 1 | 1 | 2 | 1 | 0 | 0 | " |
| 5 | 500 | 5 | 5 | 5 | 5 | 5 | 5 | 5 | 3 | 4 | " |
|   | 250 | 5 | 5 | 5 | 5 | 5 | 5 | 5 | 2 | 3 | " |
| 6 | 500 | 5 | 5 | 5 | 5 | 5 | 5 | 5 | 3 | 4 | " |
|   | 250 | 5 | 5 | 4 | 4 | 4 | 5 | 5 | 2 | 2 | " |
| 7 | 500 | 5 | 5 | 3 | 3 | 3 | 5 | 5 | 3 | 2 | " |
|   | 250 | 5 | 4 | 2 | 3 | 2 | 2 | 4 | 2 | 1 | " |
| 8 | 500 | 5 | 5 | 3 | 4 | 4 | 5 | 5 | 1 | 1 | " |
|   | 250 | 4 | 3 | 1 | 2 | 3 | 4 | 4 | 0 | 0 | " |
| 9 | 500 | 5 | 5 | 3 | 4 | 4 | 4 | 5 | 2 | 4 | " |
|   | 250 | 5 | 4 | 2 | 2 | 2 | 3 | 3 | 1 | 1 | " |
| 10 | 500 | 4 | 4 | 3 | 2 | 3 | 4 | 4 | 1 | 0 | " |
|   | 250 | 2 | 3 | 1 | 1 | 1 | 3 | 2 | 0 | 0 | " |
| 11 | 500 | 5 | 5 | 4 | 3 | 4 | 5 | 4 | 2 | 2 | " |

TABLE 2-continued

| Test Compounds | Dose (g/10a) | Growth Control Effect in Height | | | | | | | | Injury |
|---|---|---|---|---|---|---|---|---|---|---|
| | | Bentgrass | Kentucky bluegrass | Wild Lawn | Timothy | Kentucky-31 fescue | Barnyard grass | Crabgrass | Rice | Corn | |
| | 250 | 4 | 4 | 2 | 2 | 3 | 4 | 3 | 1 | 1 | " |
| Non-treated | — | 0 | 0 | 0 | 0 | 0 | 0 | 0 | 0 | 0 | — |

EXPERIMENT 2

Growth Regulating Test for Grassy Plants by Foliage Treatment

The compound of this invention formulated as in Example 2 was diluted with water and sprayed by a portable sprayer on the foliage of each of bentgrass, Kentucky bluegrass, timothy, Kentucky-31 fescue and crabgrass which had been cultivated as in Experiment 1 to have a height of 5–6 cm. The dose of the sprayed active compound was 250 g or 500 g per 10 ares. Thirty days after spraying, the height of each plant was measured and averaged.

The results are shown in Table 3.

The rating of plant growth control effect in Table 3 is the same as that illustrated in Experiment 1.

TABLE 3

| Test Compounds | Dose (g/10a) | Growth Control Effect in Height | | | | | Injury |
|---|---|---|---|---|---|---|---|
| | | Bentgrass | Kentucky bluegrass | Timothy | Kentucky-31 fescue | Crabgrass | |
| 1 | 500 | 5 | 5 | 3 | 5 | 5 | none |
| | 250 | 5 | 5 | 2 | 4 | 5 | " |
| 2 | 500 | 4 | 4 | 2 | 3 | 5 | " |
| | 250 | 3 | 3 | 2 | 2 | 4 | " |
| 4 | 500 | 4 | 4 | 3 | 3 | 4 | " |
| | 250 | 2 | 2 | 2 | 2 | 2 | " |
| 5 | 500 | 5 | 5 | 5 | 5 | 5 | " |
| | 250 | 5 | 5 | 3 | 3 | 5 | " |
| 6 | 500 | 5 | 5 | 4 | 5 | 5 | " |
| | 250 | 3 | 4 | 2 | 3 | 4 | " |
| 8 | 500 | 5 | 4 | 3 | 3 | 5 | " |
| | 250 | 4 | 4 | 2 | 3 | 4 | " |
| 10 | 500 | 4 | 4 | 2 | 3 | 4 | " |
| | 250 | 2 | 2 | 2 | 3 | 3 | " |
| Non-treated | — | 0 | 0 | 0 | 0 | 0 | — |

EXPERIMENT 3

Field Test for Lawn Growth Regulation by Foliage Treatment

Lawn which had been cultivated in a field for three years since transplantation was divided into sections of 1 m square, and mowed to a grass height of 4 cm in April when the lawn grows fast. The compound of this invention formulated as in Example 1 and diluted with water was sprayed by a sprayer at a dose of 250 g, 500 g or 1,000 g per 10 ares in terms of the active compound.

Fifteen and forty days after spraying, the height of the lawn in each section was measured.

The results are shown in Table 4 below.

TABLE 4

| Test Compounds | Dose (g/10a) | Average Height of Plant (cm) | | Injury |
|---|---|---|---|---|
| | | 15 days | 40 days | |
| 1 | 1000 | 7.2 | 12.1 | none |
| | 500 | 8.0 | 13.8 | " |
| | 250 | 8.6 | 15.2 | " |
| 5 | 1000 | 7.8 | 12.0 | " |
| | 500 | 8.6 | 15.2 | " |
| | 250 | 9.2 | 15.8 | " |
| 8 | 1000 | 8.0 | 12.6 | " |
| | 500 | 8.3 | 14.1 | " |
| | 250 | 10.2 | 17.3 | " |
| Non-treated | — | 14.2 | 22.5 | — |

EXPERIMENT 4

Unproductive Growth Inhibiting Test for Rice Seedling by Pre-emergence Soil Treatment A pot with an open area of 100 cm$^2$ was filled with clayish loam, seeded with 40 germinated grains of rice (Nihonbare strain), and lightly covered with soil. The test compound formulated as in Example 2 and diluted with water was sprayed by a portable sprayer on the soil in a dose of 250 g, 500 g, 1,000 g, or 2,000 g per 10 ares. Twenty days after spraying, the weight of the rice seedling, number of leaves, weight of foliage, and length and weight of root were measured. The test was carried out in a growth chamber with its temperature maintained in the range of from 25° to 30° C.

The results are shown in Table 5 below.

In Table 5, the figures are shown as average of 40 seedlings and the weight is on a dry basis.

TABLE 5

| Test Compounds | Dose (g/10a) | Height of plant (cm) | Root length (cm) | Number of leaves | Foliage weight (mg) | Root weight (mg) | Injury |
|---|---|---|---|---|---|---|---|
| Non-treated | — | 33.2 | 13.1 | 5 | 40.0 | 7.1 | — |
| 5 | 2000 | 16.5 | 13.2 | 5.4 | 31.8 | 10.2 | none |
| | 1000 | 20.1 | 16.3 | 5.5 | 39.2 | 10.5 | " |
| | 500 | 22.6 | 18.2 | 6.2 | 43.0 | 12.6 | " |
| | 250 | 25.4 | 19.5 | 5.3 | 41.2 | 12.5 | " |
| 6 | 2000 | 17.3 | 13.2 | 5.5 | 34.8 | 8.5 | " |

TABLE 5-continued

| Test Compounds | Dose (g/10a) | Height of plant (cm) | Root length (cm) | Number of leaves | Foliage weight (mg) | Root weight (mg) | Injury |
|---|---|---|---|---|---|---|---|
| | 1000 | 20.3 | 13.6 | 6.0 | 41.3 | 7.8 | " |
| | 500 | 20.6 | 12.9 | 6.0 | 51.3 | 9.6 | " |
| | 250 | 28.4 | 13.6 | 5.2 | 46.4 | 10.3 | " |
| 7 | 2000 | 16.8 | 12.6 | 6.0 | 36.5 | 7.2 | " |
| | 1000 | 20.5 | 13.5 | 5.4 | 39.2 | 8.5 | " |
| | 500 | 22.9 | 16.8 | 5.4 | 43.6 | 10.3 | " |
| | 250 | 24.6 | 18.5 | 5.2 | 44.0 | 9.5 | " |

This invention, particularly formulation of the growth regulator, is further illustrated by the following Examples. It should be understood that the active compounds, carriers and the mixing proportions of the formulation of this invention are not limited to the Examples. Incidentally, all parts in the Examples are by weight.

EXAMPLE 1

| Compound 1 | 30 parts |
|---|---|
| Sodium alkylsulfate | 5 parts |
| Clay | 65 parts |

The components above were mixed to make them uniform and pulverized to form wettable powder. For use this powder is diluted with water to a desired level and sprayed.

EXAMPLE 2

| Compound 5 | 10 parts |
|---|---|
| Polyoxyethylene alkylphenyl ether | 7 parts |
| Calcium alkylarylsulfonate | 3 parts |
| Xylene | 64 parts |
| Cyclohexane | 20 parts |

All the components were mixed uniformly to form an emulsifiable concentrate. For use this emulsifiable concentrate is diluted with water to a desired level and sprayed.

What is claimed is:

1. A method of stunting growth of a grassy plant, without causing phytotoxicity, which comprises applying to its foliage, or to soil containing pre-emergent seeds thereof, a compound of the formula

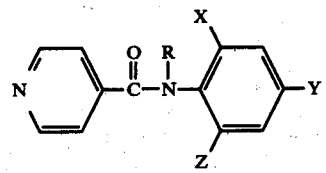

wherein R is hydrogen or lower alkyl, X is hydrogen or a halogen, Y is hydrogen, a halogen, methyl or nitro, and Z is benzoyl, in an amount of from 50 to 2,000 g per 10 ares.

2. A method according to claim 1 wherein said compound is 2-benzoyl-4-chloroisonicotinanilide.

3. A method in accordance with claim 1, wherein said amount is from 200 to 1,000 g per 10 ares.

4. A method in accordance with claim 1, wherein said grassy plant is selected from the group consisting of bentgrass, wild lawn, Kentucky bluegrass, timothy, Kentucky 31 fescue, barnyard grass, crabgrass, rice and corn.

5. A method in accordance with claim 1, wherein said grassy plant is rice and said applying step comprises applying said compound to soil containing pre-emergent rice seeds.

6. A method in accordance with claim 1, wherein, in said compound, X is hydrogen or chlorine and Y is hydrogen, chlorine, methyl or nitro.

* * * * *